United States Patent
Watts et al.

(10) Patent No.: US 9,758,792 B2
(45) Date of Patent: Sep. 12, 2017

(54) GLYPHOSATE RESISTANT CLASS 1 EPSPS GENES

(71) Applicant: SYNGENTA PARTICIPATIONS AG, Basel (CH)

(72) Inventors: Joseph M. Watts, Durham, NC (US); Sunil Ganesan, Durham, NC (US)

(73) Assignee: Syngenta Participations AG, Basel (CH)

( * ) Notice: Subject to any disclaimer, the term of this patent is extended or adjusted under 35 U.S.C. 154(b) by 42 days.

(21) Appl. No.: 14/779,052

(22) PCT Filed: Feb. 6, 2014

(86) PCT No.: PCT/US2014/014997
§ 371 (c)(1),
(2) Date: Sep. 22, 2015

(87) PCT Pub. No.: WO2014/178932
PCT Pub. Date: Nov. 6, 2014

(65) Prior Publication Data
US 2016/0186200 A1    Jun. 30, 2016

Related U.S. Application Data

(60) Provisional application No. 61/818,618, filed on May 2, 2013.

(51) Int. Cl.
| | |
|---|---|
| *C12N 15/82* | (2006.01) |
| *A01N 57/20* | (2006.01) |
| *C12N 9/10* | (2006.01) |
| *C12N 15/52* | (2006.01) |

(52) U.S. Cl.
CPC ......... *C12N 15/8275* (2013.01); *A01N 57/20* (2013.01); *C12N 9/1092* (2013.01); *C12N 15/52* (2013.01); *C12Y 205/01019* (2013.01)

(58) Field of Classification Search
None
See application file for complete search history.

(56) References Cited

U.S. PATENT DOCUMENTS

| | | | |
|---|---|---|---|
| 7,723,575 B2 | 5/2010 | Alibhai et al. | |
| 9,334,494 B2 * | 5/2016 | Basu | C12N 15/1034 |
| 2003/0027312 A1 | 2/2003 | Derose et al. | |
| 2013/0084641 A1 | 4/2013 | Basu et al. | |
| 2014/0007288 A1 | 1/2014 | Flasinski et al. | |

OTHER PUBLICATIONS

International Search Report and Written Opinion mailed Jul. 11, 2014 in International Application No. PCT/US14/14997.
Baerson et al., Plant Physiology, Jul. 2002, vol. 129, pp. 1265-1275.
Funke et al., J. Biol. Chem., 2009, vol. 284, pp. 9854-9860.

* cited by examiner

*Primary Examiner* — Eileen O Hara
(74) *Attorney, Agent, or Firm* — S. Matthew Edwards

(57) ABSTRACT

The present invention relates to DNA molecules encoding glyphosate tolerant mutant EPSPS enzymes as well as constructs and plants comprising said enzymes. Also included are methods of using said enzymes, including use as a selectable marker, use to make transgenic plants resistant to glyphosate containing herbicides and methods of controlling weeds.

19 Claims, 5 Drawing Sheets

| TIPT    | AGAEEIVLQPIKEISGTVKLPGSKSLSNRILLLAALSEGTTVVDNLLNSEDVHYMLGALP |
| TIPA    | AGAEEIVLQPIKEISGTVKLPGSKSLSNRILLLAALSEGTTVVDNLLNSELVHYMLGALR |
| TIPS    | AGAEEIVLQPIKEISGTVKLPGSKSLSNRILLLAALSEGTTVVDNLLNSELVHYMLGALR |
| maize   | AGAEEIVLQPIKEISGTVKLPGSKSLSNRILLLAALSEGTTVVENLLNSEDVHYMLGALR |
| ADGC    | AGAEEIVLQPIKEISGTVKLPGSKSLSNRILLLAALSEGTTVVENLLNSEDVHYMLGALR |
| ADGCTI  | AGAEEIVLQPIKEISGTVKLPGSKSLSNRILLLAALSEGTTVVENLLNSEDVHYMLGALR |
| ADTI    | AGAEEIVLQPIKEISGTVKLPGSKSLSNRILLLAALSEGTTVVDNLLNSEDVHYMLGALP |
|         | ************************************************ ********* |

| TIPT    | TLGLSVEADKAAKRAVVVGCGGKPPVEDAKEEVQLFLGNAGIAMRILTAAVTAAGGNATY |
| TIPA    | TLGLSVEADKAAKRAVVVGCGGKPPVEDAKEEVQLFLGNAGIAMRALTAAVTAAGGNATY |
| TIPS    | TLGLSVEALKAAKRAVVVGCGGKPFVEDAKEEVQLPLGNAGIAMRSLTAAVTAAGGNATY |
| maize   | TLGLSVEALKAAKRAVVVGCGGKFPVEDAKEEVQLPLGNAGTAMRPLTAAVTAAGGNATY |
| ADGC    | TLGLSVEDLKAAKRAVVVGCGGKFPVEDAKEEVQLPLGNACTAMRPLTAAVTAAGGNATY |
| ADGCTI  | TLGLSVEDDKAAKPAVVVGCGGKFPVEDAKEEVQLFLGNAGIAMRPLTAAVTAAGGNATY |
| ADTI    | TLGLSVEDDKAAKPAVVVGCGGKFPVEDAKEEVQLFLGNAGIAMRPLTAAVTAAGGNATY |
|         | *******  ********  **************  ***   *  *************** |

| TIPT    | VLDGVPRMRERPIGDLVVGLKQLGADVDCFLGTDCPPVRVNGIGGLPGGKVKLSGSISSQ |
| TIPA    | VLDGVPRMREPPIGDLVVGLFQLGADVDCFLGTDCPPVRVNGIGGLPGGKVKLSGSISSQ |
| TIPS    | VLDGVPRMREPPIGDLVVGLFQLGADVDCFLGTDCPPVRVNGIGGLPGGKVKLSGSISSQ |
| maize   | VLDGVPRMREPPIGDLVVGLFQLGADVDCFLGTDCPPVRVNGIGGLPGGKVKLSGSISSQ |
| ADGC    | VLDGVPRMPERPIGDLVVGLKQLGADVDCFLGTDCPPVRVNGIGGLPGGKVKLSGSISSQ |
| ADGCTI  | VLDGVPRMPERPIGDLVVGLKQLGADVDCFLGTDCPPVRVNGIGGLPGGKVKLSGSISSQ |
| ADTI    | VLDGVPRMPERPIGDLVVGLKQLGADVDCFLGTDCPPVRVNGIGGLPGGKVKLSGSISSQ |
|         | ********  ***************************************  ******** |

| TIPT    | YLSALLMAAPLALGDVEIEIIDKLISIPYVEMTLRLMERFGVKAEHSDSWDRFYIKGGQK |
| TIPA    | YLSALLMAAPLALGDVEIEIIDKLISIPYVEMTLRLMERFGVKAEHSDSWDRFYIKGGQK |
| TIPS    | YLSALLMAAPLALGDVEIEIIDKLISIPYVEMTLRLMERFGVKAEHSDSWDRFYIKGGQK |
| maize   | YLSALLMAAPLALGDVEIEIIDKLISIPYVEMTLRLMERFGVPAEHSDSWLRFYIKGGQK |
| ADGC    | YLSALLMAAPLALGDVEIEIIDKLISIPYVEMTLRLMERFGVPAEHSDSWLRFYIKGGQK |
| ADGCTI  | YLSALLMAAPLALGDVEIEIIDKLISIPYVEMTLRLMERFGVKAEHSDSWDRFYIKGGQK |
| ADTI    | YLSALLMAAPLALGDVEIEIIDKLISIPYVEMTLRLMERFGVKAEHSDSWDRFYIKGGQK |
|         | *****************************************  ****** ********* |

| TIPT    | YKSPKNAYVEGDASSASYFLAGAAITGGTVTVEGCGTTSLQGDVKFAEVLEMMGAKVTWT |
| TIPA    | YKSPKNAYVEGDASSASYFLAGAAITGGTVTVEGCGTTSLQGDVKFAEVLEMMGAKVTWT |
| TIPS    | YKSPKNAYVEGDASSASYFLAGAAITGGTVTVEGCGTTSLQGDVKFAEVLEMMGAKVTWT |
| maize   | YKSPKNAYVEGDASSASYFLAGAAITGGTVTVEGCGTTSLQGDVKFAEVLEMMGAKVTWT |
| ADGC    | YKSPKNAYVEGDASSASYFLAGAAITGGTVTVEGCGTTSLQGDVKFAEVLEMMGAKVTWT |
| ADGCTI  | YKSPKNAYVEGDASSASYFLAGAAITGGTVTVEGCGTTSLQGDVKFAEVLEMMGAKVTWT |
| ADTI    | YKSPKNAYVEGDASSASYFLAGAAITGGTVTVEGCGTTSLQGDVKFAEVLEMMGAKVTWT |
|         | *********************************************************** |

| TIPT    | ETSVTVTGPPREPFGRKHLKAIDVNMNFMPDVAMTLAVVALFADGPTAIRDVASWRVKET |
| TIPA    | ETSVTVTGPPREPFGRKHLKAIDVNMNFMPDVAMTLAVVALFADGPTAIRDVASWRVKET |
| TIPS    | ETSVTVTGPPREPFGRKHLKAIDVNMNFMPDVAMTLAVVALFADGPTAIRDVASWRVKET |
| maize   | ETSVTVTGPPPEPFGPKHLKAIDVNMNKMPDVAMTLAVVALFADGPTAIPDVASWPVKET |
| ADGC    | ETSVTVTGPPPEPFGPKHLKAIDVNMNKMPDVAMTLAVVALFADGPTAIPDVASWPVKET |
| ADGCTI  | ETSVTVTGPPPEPFGPKHLKAIDVNMNKMPDVAMTLAVVALFADGPTAIPDVASWPVKET |
| ADTI    | ETSVTVTGPPREPFGRKHLKAIDVNMNFMPDVAMTLAVVALFADGPTAIRDVASWRVKET |
|         | ********** *** ***********  ********************  ****  **** |

| TIPT    | ERNVAIPTELTKLGASVEEGPDYCIITPPEKLNVTAIDTYDDHRMAMAFSLAACAEVPVT |
| TIPA    | ERNVAIPTELTKLGASVEEGPDYCIITPPEKLNVTAIDTYDDHRMAMAFSLAACAEVPVT |
| TIPS    | ERNVAIRTELTKLGASVEEGPDYCIITPPEKLNVTAIDTYDDHRMAMAFSLAACAEVPVT |
| maize   | ERNVAIRTELTKLGASVEEGPDYCIITPPEKLNVTAIDTYDDHRMAMAFSLAACAEVPVT |
| ADGC    | ERNVAIRTELTKLGASVEEGPDYCIITPPEKLNVTAIDTYDDHRMAMAFSLAACAEVPVT |
| ADGCTI  | ERNVAIRTELTKLGASVEEGPDYCIITPPEKLNVTAIDTYDDHRMAMAFSLAACAEVPVT |

FIG. 1A

```
ADTI        ERMVAIRTELTKLGASVEEGPDYCIITPPEKLNVTAIDTYDDRMAMAFSLAACAEVPVT
            ************************************************************

TIPT        IRDPGCTRKTFPDYFDVLSTFVKN
TIPA        IRDPGCTRKTFPDYFDVLSTFVKN
TIPS        IRDPGCTRKTFPDYFDVLSTFVKN
maize       IRDPGCTRKTFPDYFDVLSTFVKN
ADGC        IRDPGCTRKTFPDYFDVLSTFVKN
ADGCTI      IRDPGCTRKTFPDYFDVLSTFVKN
ADTI        IRDPGCTRKTFPDYFDVLSTFVKN
            ************************
```

FIG. 1B

```
petunia    ---ATAQKPSEIVLQPIKEISGTVKLPGSKSLSNRILLLAALSEGTTVVDNLLSSEDIHY
soybean    AAAEKPSTAPEIVLEPIKDISGTITLPGSKSLSNRILLLAALSEGTTVVDKLLYSEDIHY
maize      ------AGAEEIVLQPIKEISGTVKLPGSKSNRILLLAALSEGTTVVDNLLNSEDVHY
E. coli    --------MESLTLQPIARVDGTINLPGSKSVSNRALLLAALAHGKTVLTNLLDSDDVRH
                   .:.*;**  ;.**;.***;****;*:*:****;.*.*:; *** *;*:;;

petunia    MLGALKTLGLHVEEDSANQRAVVEGCGGLFPVGKESKEEIQLFLGNAGTAMRPLTAAVTV
soybean    MLGALRTLGLRVEDDNTTKQAIVEGCGGLFPTIKESKDEINLPLGNAGTAMRPLTAAVVA
maize      MLGALRTLGLSVEADKAAKPAVVVGCGGKFPVED-AKEEVQLFLGNAGTAMRPLTAAVTA
E. coli    MLNALTALGVSYTLSADRIPCEIIGNGGPLHAEG----ALELFLGNAGTAMRPLAAALCL
           **.**.;**;         .   ;. ; * ** ;.;      ;;********;**;

petunia    AGGNSRYVLDGVPRMRERPISDLVDGLKQL-GAEVDCFLGTFKCPPVPIVSKGGLPGGKVKL
soybean    AGGNASIYVLDGVPRMRERPIGDLVAGLKQLGADVDCFLGTMCPPVRVNGKGGLPGGKVKL
maize      AGGNATYVLDGVPRMRERPIGDLVVGLKQLGADVDCFLGTDCPPVRVNGIGGLPGGKVKL
E. coli    GSND--IVLTGEPRMKERPIGHLVDALRLGGASITYLEQENYPPLRLQG--GPTGGNVIV
           .,.;    ;**   *  ***;**.;** .*;  **.;    ;     .   *;.**:*.;

petunia    SGSISSQYLTALLMAAPLALGDVEIEIIDKLISVPYVEMTLKLMERFGISVEHSSSWDRF
soybean    SGSVSSQYLTALLMAAPLALGDVEIEIIVDKLISVPYVEMTLKLMERFGVSVEHSGNWDRF
maize      SGSISSQYLSALLMAAPLALGDVEIEIIDKLISIPYVEMTLRLMERFGVKAEHSDSWDRF
E. coli    DGSVSSQFLTALLMTAPLAPEDTVIRIKGDLVSKPYIDITLNLMKTFGVEIEN-QHYQQF
           ;;*:*;***;**  *  *.;* ;.;.* ;;.;; * *;   ;;;* petunia    PVRGGQKYKSPGKAFVEGDASSASYFLAGAAVTGGTITVEGCGTNSLQGDVKFAEVLERM
soybean    LVRGGQKYKSPGNAFVEGDASSASYLLAGAAITGGTITVNGCGTSSLQGDVKFAEVLERM
maize      YIKGGQKYKSPKNAYVEGDASSASYFLAGAAITGGYVTVEGCGTTSLQGDVKFAEVLESN
E. coli    VVKGGQSYQSPGTYLVEGDASSASYFLAAAAIKGGTVKVTGIGRNSMQGDIRFADVLEKM
           ;;;***.*;;   . ******;.;.*;.* *  .*;*;;;**  * petunia    GAEVTWTENSVTVKGPPRSSGRKHLRAIDVNMNKMPDVAMTLAVVALYADGPTAIRDVA
soybean    GAKVTWSENSVTVSGPPRDFSGPKVLRGILVRMNKMPDVAMTLAVVALFANGPTAIRDVA
maize      GAKVTWTETSVTVTGPPREFFGPKHLKAIDVRMNYMPDVAMTLAVVALFADGPTAIRDVA
E. coli    GATICWGDDYISCT--------RGELNAIDMDMNHIPDAAMTIATAALFAKGTTTLRNIY
           **.;.*.;.  ;;.        . *.*,*;****;.*.**;**,***;*;.*.*;;*;;

petunia    SWRVKETERNIAICTELRKLGATVEEGPDYCIITPPEKLNVTDIDTYDDHRMAMAFSLAA
soybean    SWRVKETERNIAICTELRKLGATVEEGPDYCVITPPEKLNVTAILTYDDHRMAMAFSLAA
maize      SWRVKETERNVAIRTELTKLGASVEEGPDYCIITPPEKLNVTAILTYDDHRMAMAFSLAA
E. coli    NWRVKETDRLFAMATELRKVGAEVEEGHDYIPITPPEKLNFAEIATYNDHRMAMCFSLVA
           ;******;*;.*;.* *.**.. ********;.  * *;***.*.* petunia    CADVPVTINDPGCTRKTFENYFQVLQQYSKHN
soybean    CGDVPVTIKDPGCTRKTFPDYFEVLERLTKH-
maize      CAEVPVTIRDPGCTRKIFPDYFDVLSTFVKN-
E. coli    LSDTPVTILDPKCTAKTFPDYFEQLARISQAA
             .;.****  ** **.***; **  *   ;
```

FIG. 2

SEQUENCE LISTING

<160> NUMBER OF SEQ ID NOS: 14

<210> SEQ ID NO 1
<211> LENGTH: 1335
<212> TYPE: DNA
<213> ORGANISM: Zea mays

<400> SEQUENCE: 1

```
gctggtgcta aagaaattgt gctccaacct atcaaagaga tctccggaac tgttaagctc        60
ccaggatcta agtctctcag caacaggatt cttcttcttg ctgctttgtc tgagggaact       120
accgttgttg ataaccttct taactccgag gacgtgcact atatgcttgg tgctcttaga       180
acccttggac tttctgttga agctgataag gctgctaaga gggctgttgt tgttggatgc       240
ggaggaaagt tcccagttga agatgctaaa gaagaggtgc agcttttcct tggaaacgct       300
ggaactgcta tgaggccact tactgctgct gttaccgctg ctggtggaaa cgctacttat       360
gttcttgatg gtgttcccag aatgagagaa aggccaattg gagatcttgt ggttggactt       420
aagcagcttg gagctgatgt tgattgcttc cttggaactg attgcccacc agttagggtt       480
aacggaattg gaggacttcc aggtggaaag gttaagcttt ctggatctat ttcctcccag       540
tacctttctg ctcttttgat ggctgctcca cttgctcttg gagatgttga gattgagatc       600
atcgacaagc tcatctccat cccatacgtt gagatgactc ttaggctcat ggaaaggttc       660
ggagttaagg ctgagcattc tgattcttgg gacaggttct acattaaggg tggacagaag       720
tacaagtccc caagaacgc ttatgttgag ggtgatgctt ctagtgcttc ttatttcctt       780
gctggtgctg ctattactgg tggaactgtt actgttgaag gatgcggaac tacttctctt       840
cagggtgatg ttaagttcgc tgaggttttg gaaatgatgg gagctaaggt tacctggact       900
gagacttctg ttactgttac tggaccacca agagaaccat tcggaagaaa gcacctcaag       960
gctattgacg tgaacatgaa caagatgcca gatgttgcta tgaccttgc tgttgttgct      1020 cttttcgctg atggaccaac tgctattagg gatgttgctt cttggagggt gaaagaaact      1080
gagaggatgg ttgctattag gactgagctt actaagcttg gagcttctgt tgaggaagga      1140
```

```
ccagattact gcattattac tccacccgag aagcttaacg tgaccgctat tgatacctac    1200
gatgatcata ggatggctat ggcttttctct ttggctgctt gcgctgaagt tccagttact    1260
attagagatc caggctgcac tagaaagacc ttcccagatt acttcgatgt gctttctacc    1320
ttcgtgaaga actga                                                     1335
```

```
<210> SEQ ID NO 2
<211> LENGTH: 1335
<212> TYPE: DNA
<213> ORGANISM: Artificial sequence
<220> FEATURE:
<223> OTHER INFORMATION: Mutated Zea mays
<220> FEATURE:
<221> NAME/KEY: misc_feature
<222> LOCATION: (204)..(204)
<223> OTHER INFORMATION: n = a or t
```

```
<400> SEQUENCE: 2
gctggtgctg aagaaattgt gctccaacct atcaaagaga tctccggaac tgttaagctc     60
ccaggatcta agtctctcag caacaggatt cttcttcttg ctgctttgtc tgagggaact   120
accgttgttg ataaccttct taactccgag gacgtgcact atatgcttgg tgctcttaga   180
acccttggac tttctgttga agangataag gctgctaaga gggctgttgt tgttggatgc   240
ggaggaaagt tcccagttga agatgctaaa gaagaggtgc agcttttcct tggaaacgct   300
ggaattgcta tgaggccact tactgctgct gttaccgctg ctggtggaaa cgctacttat   360
gttcttgatg gtgttcccag aatgagagaa aggccaattg agatcttgt ggttggactt   420 aagcagcttg gagctgatgt tgattgcttc cttggaactg attgcccacc agttagggtt   480
aacggaattg gaggacttcc aggtggaaag gttaagcttt ctggatctat ttcctcccag   540
tacctttctg ctctttttgat ggctgctcca cttgctcttg gagatgttga gattgagatc   600
atcgacaagc tcatctccat cccatacgtt gagatgactc ttaggctcat ggaaaggttc   660
ggagttaagg ctgagcattc tgattcttgg gacaggttct acattaaggg tggacagaag   720
tacaagtccc caagaacgc ttatgttgag ggtgatgctt ctagtgcttc ttatttcctt   780
gctggtgctg ctattactgg tggaactgtt actgttgaag gatgcggaac tacttctctt   840
cagggtgatg ttaagttcgc tgaggttttg gaaatgatgg gagctaaggt tacctggact   900
gagacttctg ttactgttac tggaccacca agagaaccat tcggaagaaa gcacctcaag   960
gctattgacg tgaacatgaa caagatgcca gatgttgcta tgacccttgc tgttgttgct  1020
cttttcgctg atggaccaac tgctattagg gatgttgctt cttggagggt gaaagaaact  1080
gagaggatgg ttgctattag gactgagctt actaagcttg gagcttctgt tgaggaagga  1140
ccagattact gcattattac tccacccgag aagcttaacg tgaccgctat tgatacctac  1200
gatgatcata ggatggctat ggcttttctct ttggctgctt gcgctgaagt tccagttact  1260
attagagatc caggctgcac tagaaagacc ttcccagatt acttcgatgt gctttctacc  1320
ttcgtgaaga actga                                                   1335
```

```
<210> SEQ ID NO 3
<211> LENGTH: 1335
<212> TYPE: DNA
<213> ORGANISM: Artificial sequence
<220> FEATURE:
<223> OTHER INFORMATION: Mutated zea mays
<220> FEATURE:
<221> NAME/KEY: misc_feature
<222> LOCATION: (204)..(204)
<223> OTHER INFORMATION: n = t or a
```

<400> SEQUENCE: 3

```
gctggtgctg aagaaattgt gctccaacct atcaaagaga tctccggaac tgttaagctc      60
ccaggatcta agtctctcag caacaggatt cttcttcttg ctgctttgtc tgagggaact     120
accgttgttg ataaccttct taactccgag gacgtgcact atatgcttgg tgctcttaga     180
acccttggac tttctgttga agangataag gctgctaaga gggctgttgt tgttggatgc     240
ggaggaaagt tcccagttga agatgctaaa gaagaggtgc agcttttcct tggaaacgct     300
tgcactgcta tgaggccact tactgctgct gttaccgctg ctggtggaaa cgctacttat     360
gttcttgatg gtgttcccag aatgagagaa aggccaattg agatcttgt ggttggactt      420
aagcagcttg gagctgatgt tgattgcttc cttggaactg attgcccacc agttagggtt     480
aacggaattg gaggacttcc agtgggaaag gttaagcttt ctggatctat ttcctcccag     540
tacctttctg ctcttttgat ggctgctcca cttgctcttg gagatgttga gattgagatc     600
atcgacaagc tcatctccat cccatacgtt gagatgactc ttaggctcat ggaaaggttc     660
ggagttaagg ctgagcattc tgattcttgg acaggttct acattaaggg tggacagaag      720
tacaagtccc caaagaacgc ttatgttgag ggtgatgctt ctagtgcttc ttatttcctt     780
gctggtgctg ctattactgg tggaactgtt actgttgaag gatgcggaac tacttctctt     840
cagggtgatg ttaagttcgc tgaggttttg gaaatgatgg gagctaaggt tacctggact     900
gagacttctg ttactgttac tggaccacca agagaaccat tcggaagaaa gcacctcaag     960
gctattgacg tgaacatgaa caagatgcca atgttgcta tgaccctttgc tgttgttgct    1020
cttttcgctg atggaccaac tgctattagg gatgttgctt cttggagggt gaaagaaact    1080
gagaggatgg ttgctattag gactgagctt actaagcttg gagcttctgt tgaggaagga    1140
ccagattact gcattattac tccacccgag aagcttaacg tgaccgctat tgatacctac    1200
gatgatcata ggatggctat ggctttctct ttggctgctt gcgctgaagt tccagttact    1260
attagagatc caggctgcac tagaaaagacc ttcccagatt acttcgatgt gctttctacc   1320
ttcgtgaaga actga                                                     1335
```

<210> SEQ ID NO 4
<211> LENGTH: 1335
<212> TYPE: DNA
<213> ORGANISM: Artificial sequence
<220> FEATURE:
<223> OTHER INFORMATION: Mutated zea mays
<220> FEATURE:
<221> NAME/KEY: misc_feature
<222> LOCATION: (204)..(204)
<223> OTHER INFORMATION: n = t or a

<400> SEQUENCE: 4

```
gctggtgctg aagaaattgt gctccaacct atcaaagaga tctccggaac tgttaagctc      60
ccaggatcta agtctctcag caacaggatt cttcttcttg ctgctttgtc tgagggaact     120
accgttgttg ataaccttct taactccgag gacgtgcact atatgcttgg tgctcttaga     180
acccttggac tttctgttga agangataag gctgctaaga gggctgttgt tgttggatgc     240
ggaggaaagt tcccagttga agatgctaaa gaagaggtgc agcttttcct tggaaacgct     300
tgcattgcta tgaggccact tactgctgct gttaccgctg ctggtggaaa cgctacttat     360
gttcttgatg gtgttcccag aatgagagaa aggccaattg agatcttgt ggttggactt      420
aagcagcttg gagctgatgt tgattgcttc cttggaactg attgcccacc agttagggtt     480
```

```
aacggaattg gaggacttcc aggtggaaag gttaagcttt ctggatctat ttcctcccag      540
tacctttctg ctcttttgat ggctgctcca cttgctcttg agatgttgga gattgagatc      600
atcgacaagc tcatctccat cccatacgtt gagatgactc ttaggctcat ggaaaggttc      660
ggagttaagg ctgagcattc tgattcttgg acaggttct acattagggg tggacagaag       720
tacaagtccc caagaacgc ttatgttgag ggtgatgctt ctagtgcttc ttatttcctt       780
gctggtgctg ctattactgg tggaactgtt actgttgaag gatgcggaac tacttctctt      840
cagggtgatg ttaagttcgc tgaggttttg gaaatgatgg gagctaaggt tacctggact      900
gagacttctg ttactgttac tggaccacca agagaaccat tcggaagaaa gcacctcaag      960
gctattgacg tgaacatgaa caagatgcca gatgttgcta tgaccttgc tgttgttgct      1020 cttttcgctg atggaccaac tgctattagg gatgttgctt cttggagggt gaaagaaact     1080
gagaggatgg ttgctattag gactgagctt actaagcttg gagcttctgt tgaggaagga     1140
ccagattact gcattattac tccacccgag aagcttaacg tgaccgctat tgataccac       1200 gatgatcata ggatggctat ggcttttctct ttggctgctt cgctgaagt tccagttact      1260 attagagatc caggctgcac tagaaagacc ttcccagatt acttcgatgt gctttctacc     1320
ttcgtgaaga actga                                                       1335
```

<210> SEQ ID NO 5  
<211> LENGTH: 444  
<212> TYPE: PRT  
<213> ORGANISM: Zea mays

<400> SEQUENCE: 5

```
Ala Gly Ala Glu Glu Ile Val Leu Gln Pro Ile Lys Glu Ile Ser Gly
 1               5                  10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220
```

-continued

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440

<210> SEQ ID NO 6
<211> LENGTH: 444
<212> TYPE: PRT
<213> ORGANISM: Artificial sequence
<220> FEATURE:
<223> OTHER INFORMATION: Mutated zea mays
<220> FEATURE:
<221> NAME/KEY: MISC_FEATURE
<222> LOCATION: (68)..(68)
<223> OTHER INFORMATION: X = D or E

<400> SEQUENCE: 6

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Xaa Asp Lys Ala Ala Lys Arg Ala Val Val Val Gly Cys
65                  70                  75                  80

Gly Gly Lys Phe Pro Val Glu Asp Ala Lys Glu Val Gln Leu Phe
                85                  90                  95

Leu Gly Asn Ala Gly Ile Ala Met Arg Pro Leu Thr Ala Ala Val Thr
            100                 105                 110

Ala Ala Gly Gly Asn Ala Thr Tyr Val Leu Asp Gly Val Pro Arg Met

```
            115                 120                 125
Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440

<210> SEQ ID NO 7
<211> LENGTH: 444
<212> TYPE: PRT
<213> ORGANISM: Artificial sequence
<220> FEATURE:
<223> OTHER INFORMATION: Mutated zea mays
<220> FEATURE:
<221> NAME/KEY: MISC_FEATURE
<222> LOCATION: (68)..(68)
<223> OTHER INFORMATION: X = D or E

<400> SEQUENCE: 7

Ala Gly Ala Glu Glu Ile Val Leu Gln Pro Ile Lys Glu Ile Ser Gly
1               5                   10                  15
```

```
Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Xaa Asp Lys Ala Ala Lys Arg Ala Val Val Gly Cys
65                  70                  75                  80

Gly Gly Lys Phe Pro Val Glu Asp Ala Lys Glu Val Gln Leu Phe
                85                  90                  95

Leu Gly Asn Ala Cys Thr Ala Met Arg Pro Leu Thr Ala Ala Val Thr
            100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
            130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
            195                 200                 205

Tyr Val Glu Met Thr Leu Arg Leu Met Glu Arg Phe Gly Val Lys Ala
            210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
            275                 280                 285

Val Leu Glu Met Met Gly Ala Lys Val Thr Trp Thr Glu Thr Ser Val
            290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
            325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
            355                 360                 365

Glu Leu Thr Lys Leu Gly Ala Ser Val Glu Glu Gly Pro Asp Tyr Cys
            370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
```

<210> SEQ ID NO 8
<211> LENGTH: 444
<212> TYPE: PRT
<213> ORGANISM: Artificial sequence
<220> FEATURE:
<223> OTHER INFORMATION: Mutated zea mays
<220> FEATURE:
<221> NAME/KEY: MISC_FEATURE
<222> LOCATION: (68)..(68)
<223> OTHER INFORMATION: X = D or E

<400> SEQUENCE: 8

```
Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Xaa Asp Lys Ala Ala Lys Arg Ala Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Cys Ile Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335
```

```
Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
            435                 440

<210> SEQ ID NO 9
<211> LENGTH: 444
<212> TYPE: PRT
<213> ORGANISM: Artificial sequence
<220> FEATURE:
<223> OTHER INFORMATION: Mutated Zea mays

<400> SEQUENCE: 9

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Val Gln Leu Phe
            85                  90                  95

Leu Gly Asn Ala Gly Ile Ala Met Arg Thr Leu Thr Ala Ala Val Thr
        100                 105                 110

Ala Ala Gly Gly Asn Ala Thr Tyr Val Leu Asp Gly Val Pro Arg Met
    115                 120                 125

Arg Glu Arg Pro Ile Gly Asp Leu Val Val Gly Leu Lys Gln Leu Gly
130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255
```

```
Ser Tyr Phe Leu Ala Gly Ala Ile Thr Gly Thr Val Thr Val
            260                 265                 270

Glu Gly Cys Gly Thr Thr Ser Leu Gln Gly Asp Val Lys Phe Ala Glu
            275                 280                 285

Val Leu Glu Met Met Gly Ala Lys Val Thr Trp Thr Glu Thr Ser Val
            290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
            355                 360                 365

Glu Leu Thr Lys Leu Gly Ala Ser Val Glu Glu Gly Pro Asp Tyr Cys
            370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
            435                 440

<210> SEQ ID NO 10
<211> LENGTH: 444
<212> TYPE: PRT
<213> ORGANISM: Artificial sequence
<220> FEATURE:
<223> OTHER INFORMATION: Mutated Zea mays

<400> SEQUENCE: 10

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
            35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Ile Ala Met Arg Ala Leu Thr Ala Ala Val Thr
            100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175
```

```
Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440

<210> SEQ ID NO 11
<211> LENGTH: 444
<212> TYPE: PRT
<213> ORGANISM: Artificial sequence
<220> FEATURE:
<223> OTHER INFORMATION: Mutated Zea mays

<400> SEQUENCE: 11

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95
```

-continued

```
Leu Gly Asn Ala Gly Ile Ala Met Arg Ser Leu Thr Ala Ala Val Thr
                100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
        130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440

<210> SEQ ID NO 12
<211> LENGTH: 451
<212> TYPE: PRT
<213> ORGANISM: Glycine max

<400> SEQUENCE: 12

Ala Ala Ala Glu Lys Pro Ser Thr Ala Pro Glu Ile Val Leu Glu Pro
1               5                   10                  15

Ile Lys Asp Ile Ser Gly Thr Ile Thr Leu Pro Gly Ser Lys Ser Leu
            20                  25                  30
```

```
Ser Asn Arg Ile Leu Leu Ala Ala Leu Ser Glu Gly Thr Thr Val
        35                  40                  45

Val Asp Asn Leu Leu Tyr Ser Glu Asp Ile His Tyr Met Leu Gly Ala
    50                  55                  60

Leu Arg Thr Leu Gly Leu Arg Val Glu Asp Asp Lys Thr Thr Lys Gln
65                  70                  75                  80

Ala Ile Val Glu Gly Cys Gly Gly Leu Phe Pro Thr Ile Lys Glu Ser
                85                  90                  95

Lys Asp Glu Ile Asn Leu Phe Leu Gly Asn Ala Gly Thr Ala Met Arg
                100                 105                 110

Pro Leu Thr Ala Ala Val Val Ala Ala Gly Gly Asn Ala Ser Tyr Val
                115                 120                 125

Leu Asp Gly Val Pro Arg Met Arg Glu Arg Pro Ile Gly Asp Leu Val
                130                 135                 140

Ala Gly Leu Lys Gln Leu Gly Ala Asp Val Asp Cys Phe Leu Gly Thr
145                 150                 155                 160

Asn Cys Pro Pro Val Arg Val Asn Gly Lys Gly Gly Leu Pro Gly Gly
                165                 170                 175

Lys Val Lys Leu Ser Gly Ser Val Ser Ser Gln Tyr Leu Thr Ala Leu
                180                 185                 190

Leu Met Ala Ala Pro Leu Ala Leu Gly Asp Val Glu Ile Glu Ile Val
                195                 200                 205

Asp Lys Leu Ile Ser Val Pro Tyr Val Glu Met Thr Leu Lys Leu Met
                210                 215                 220

Glu Arg Phe Gly Val Ser Val Glu His Ser Gly Asn Trp Asp Arg Phe
225                 230                 235                 240

Leu Val His Gly Gly Gln Lys Tyr Lys Ser Pro Gly Asn Ala Phe Val
                245                 250                 255

Glu Gly Asp Ala Ser Ser Ala Ser Tyr Leu Leu Ala Gly Ala Ala Ile
                260                 265                 270

Thr Gly Gly Thr Ile Thr Val Asn Gly Cys Gly Thr Ser Ser Leu Gln
                275                 280                 285

Gly Asp Val Lys Phe Ala Glu Val Leu Glu Lys Met Gly Ala Lys Val
                290                 295                 300

Thr Trp Ser Glu Asn Ser Val Thr Val Ser Gly Pro Pro Arg Asp Phe
305                 310                 315                 320

Ser Gly Arg Lys Val Leu Arg Gly Ile Asp Val Asn Met Asn Lys Met
                325                 330                 335

Pro Asp Val Ala Met Thr Leu Ala Val Val Ala Leu Phe Ala Asn Gly
                340                 345                 350

Pro Thr Ala Ile Arg Asp Val Ala Ser Trp Arg Val Lys Glu Thr Glu
                355                 360                 365

Arg Met Ile Ala Ile Cys Thr Glu Leu Arg Lys Leu Gly Ala Thr Val
                370                 375                 380

Glu Glu Gly Pro Asp Tyr Cys Val Ile Thr Pro Glu Lys Leu Asn
385                 390                 395                 400

Val Thr Ala Ile Asp Thr Tyr Asp Asp His Arg Met Ala Met Ala Phe
                405                 410                 415

Ser Leu Ala Ala Cys Gly Asp Val Pro Val Thr Ile Lys Asp Pro Gly
                420                 425                 430

Cys Thr Arg Lys Thr Phe Pro Asp Tyr Phe Glu Val Leu Glu Arg Leu
                435                 440                 445
```

Thr Lys His
    450

<210> SEQ ID NO 13
<211> LENGTH: 427
<212> TYPE: PRT
<213> ORGANISM: Escherichia coli

<400> SEQUENCE: 13

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

```
Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
                420                 425
```

<210> SEQ ID NO 14
<211> LENGTH: 448
<212> TYPE: PRT
<213> ORGANISM: Petunia x hybrida

<400> SEQUENCE: 14

```
Ala Thr Ala Gln Lys Pro Ser Glu Ile Val Leu Gln Pro Ile Lys Glu
1               5                   10                  15

Ile Ser Gly Thr Val Lys Leu Pro Gly Ser Lys Ser Leu Ser Asn Arg
                20                  25                  30

Ile Leu Leu Leu Ala Ala Leu Ser Glu Gly Thr Thr Val Val Asp Asn
                35                  40                  45

Leu Leu Ser Ser Asp Asp Ile His Tyr Met Leu Gly Ala Leu Lys Thr
50              55                  60

Leu Gly Leu His Val Glu Asp Ser Ala Asn Gln Arg Ala Val Val
65                  70                  75                  80

Glu Gly Cys Gly Gly Leu Phe Pro Val Gly Lys Glu Ser Lys Glu Glu
                85                  90                  95

Ile Gln Leu Phe Leu Gly Asn Ala Gly Thr Ala Met Arg Pro Leu Thr
                100                 105                 110

Ala Ala Val Thr Val Ala Gly Gly Asn Ser Arg Tyr Val Leu Asp Gly
                115                 120                 125

Val Pro Arg Met Arg Glu Arg Pro Ile Ser Asp Leu Val Asp Gly Leu
                130                 135                 140

Lys Gln Leu Gly Ala Glu Val Asp Cys Phe Leu Gly Thr Lys Cys Pro
145                 150                 155                 160

Pro Val Arg Ile Val Ser Lys Gly Gly Leu Pro Gly Gly Lys Val Lys
                165                 170                 175

Leu Ser Gly Ser Ile Ser Ser Gln Tyr Leu Thr Ala Leu Leu Met Ala
                180                 185                 190

Ala Pro Leu Ala Leu Gly Asp Val Glu Ile Glu Ile Asp Lys Leu
                195                 200                 205

Ile Ser Val Pro Tyr Val Glu Met Thr Leu Lys Leu Met Glu Arg Phe
210                 215                 220

Gly Ile Ser Val Glu His Ser Ser Ser Trp Asp Arg Phe Phe Val Arg
225                 230                 235                 240

Gly Gly Gln Lys Tyr Lys Ser Pro Gly Lys Ala Phe Val Glu Gly Asp
                245                 250                 255

Ala Ser Ser Ala Ser Tyr Phe Leu Ala Gly Ala Ala Val Thr Gly Gly
                260                 265                 270

Thr Ile Thr Val Glu Gly Cys Gly Thr Asn Ser Leu Gln Gly Asp Val
                275                 280                 285

Lys Phe Ala Glu Val Leu Glu Lys Met Gly Ala Glu Val Thr Trp Thr
                290                 295                 300

Glu Asn Ser Val Thr Val Lys Gly Pro Pro Arg Ser Ser Ser Gly Arg
```

-continued

```
        305                 310                 315                 320
Lys His Leu Arg Ala Ile Asp Val Asn Met Asn Lys Met Pro Asp Val
                325                 330                 335

Ala Met Thr Leu Ala Val Val Ala Leu Tyr Ala Asp Gly Pro Thr Ala
                340                 345                 350

Ile Arg Asp Val Ala Ser Trp Arg Val Lys Glu Thr Glu Arg Met Ile
                355                 360                 365

Ala Ile Cys Thr Glu Leu Arg Lys Leu Gly Ala Thr Val Glu Glu Gly
            370                 375                 380

Pro Asp Tyr Cys Ile Ile Thr Pro Pro Glu Lys Leu Asn Val Thr Asp
385                 390                 395                 400

Ile Asp Thr Tyr Asp Asp His Arg Met Ala Met Ala Phe Ser Leu Ala
                405                 410                 415

Cys Ala Asp Val Pro Val Thr Ile Asn Asp Pro Gly Cys Thr Arg Lys
                420                 425                 430

Thr Phe Pro Asn Tyr Phe Asp Val Leu Gln Gln Tyr Ser Lys His Asn
                435                 440                 445
```

GLYPHOSATE RESISTANT CLASS 1 EPSPS GENES

STATEMENT REGARDING ELECTRONIC SUBMISSION OF A SEQUENCE LISTING

A Sequence Listing in ASCII text format, submitted under 37 C.F.R. §1.821, entitled "73585-US-L-ORG-NAT_ST25.txt", 23,723 bytes in size, generated on May 2, 2013 and filed via EFS-Web is provided in lieu of a paper copy. This Sequence Listing is hereby incorporated by reference into the specification for its disclosures.

FIELD OF THE INVENTION

This invention relates to genes for providing herbicide resistance in plants and, more particularly, to class I 5-enolpyruvylshikimate-3-phosphate synthases (EPSPSs) modified to provide glyphosate resistance, and variants thereof. More specifically, the invention comprises DNA and protein compositions of glyphosate resistant EPSPS genes, methods of use in plant cell culture, crop breeding, creation of transgenic plants, controlling weeds at a locus comprising the transgenic plants and to the transgenic plants comprising the EPSPS DNA.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSPS") kills plant cells by shutting down the shikimate pathway, thereby inhibiting aromatic amino acid biosynthesis. Inhibition of aromatic amino acid biosynthesis kills plant cells as well as some bacterial cells. Glyphosate is an effective, broad-spectrum systemic herbicide used to kill weeds and is the most widely used herbicide in the United States.

EPSPS enzymes are broadly categorized into three groups: Class I, Class II and Class Ill. Mutations in Class I EPSPS genes are known that provide tolerance to glyphosate's inhibitory activity. For example, Glyphosate tolerance in plants can be achieved by the expression of a modified Class I EPSPS that has lower affinity for glyphosate, yet still retains its catalytic activity in the presence of glyphosate (U.S. Pat. Nos. 4,535,060, 6,040,497, and 7,723,575). "Tolerate", "tolerance", "resist" or "resistance" is intended to mean that a plant can either survive, or carry out essential cellular functions such as protein synthesis and respiration in the presence of an herbicide, particularly glyphosate, in a manner that is not readily discernible from untreated cells. Class I EPSPS genes can be found in a variety of backgrounds, including plants, algae and microorganism such as bacteria. Well-known Class I genes are derived from *Zea mays* (corn) and *E. coli* (where the gene is known as aroA).

Class II and Class III EPSPSs have been isolated from bacteria that are naturally resistant to glyphosate and when the enzyme is expressed as a transgene in plants provides glyphosate tolerance to the plants (Ex. U.S. Pat. Nos. 5,633,435, 5,094,945 and 7,534,937).

Crop plants that comprise one of the tolerant EPSPSs from Class I, II or III are tolerant to glyphosate and allow glyphosate to be used for effective weed control with minimal concern of crop damage. For example, glyphosate tolerance has been genetically engineered into corn (U.S. Pat. No. 5,554,798), wheat (Zhou et al. Plant Cell Rep. 15:159-163, 1995), soybean (WO 9200377), sugarbeet (U.S. Pat. No. 7,335,816), and canola (WO 9204449).

There is a great need in plant molecular biology for a diversity of genes that can provide a selectable marker phenotype. Tolerant EPSPS enzymes are useful as selectable markers during transformation where glyphosate selection is used, i.e. where transformed plant cells comprising the tolerant EPSPS are selected due to their ability to survive on glyphosate-containing media. The present invention provides DNA and protein compositions of a glyphosate tolerant variant Class I EPSPS enzyme. The present invention also provides DNA constructs useful in plants and transgenic plants that exhibit glyphosate tolerance.

SUMMARY OF THE INVENTION

In one aspect of the invention there is provided an isolated modified EPSPS DNA molecule encoding a glyphosate tolerant EPSPS protein having an aspartic acid at position 68, and an isoleucine or leucine at position 102. In another aspect of the invention there is provided an isolated modified EPSPS DNA molecule encoding a glyphosate tolerant EPSPS protein having a glutamic acid at position 68, and a cysteine at position 101.

In another aspect of the invention is a DNA construct that comprises a promoter that functions in plant cells operably linked to a modified EPSPS DNA molecule encoding a glyphosate tolerant EPSPS protein having an aspartic acid at position 68, and an isoleucine or leucine at position 102. In yet another aspect of the invention there is provided a transgenic plant than contains the DNA construct, wherein the transgenic plant is tolerant to glyphosate herbicide.

In another aspect of the invention is a DNA construct that comprises a promoter that functions in plant cells operably linked to a modified EPSPS DNA molecule encoding a glyphosate tolerant EPSPS protein having a glutamic acid at position 68, and a cysteine at position 101. In yet another aspect of the invention there is provided a transgenic plant than contains the DNA construct, wherein the transgenic plant is tolerant to glyphosate herbicide.

In another aspect of the invention is a method of preparing a fertile transgenic plant comprising providing a plant expression cassette having a modified EPSPS gene encoding an EPSPS protein having an aspartic acid at position 68, and an isoleucine or leucine at position 102; and contacting recipient plant cells with the plant expression cassette under conditions permitting the uptake of the plant expression cassette by the recipient cells; and selecting the recipient plant cells that contain the plant expression cassette; and regenerating plants from the selected recipient plant cells; and identifying a fertile transgenic plant that is tolerant to glyphosate.

In another aspect of the invention is a method of preparing a fertile transgenic plant comprising providing a plant expression cassette having a modified EPSPS gene encoding an EPSPS protein having a glutamic acid at position 68, and a cysteine at position 101; and contacting recipient plant cells with the plant expression cassette under conditions permitting the uptake of the plant expression cassette by the recipient cells; and selecting the recipient plant cells that contain the plant expression cassette; and regenerating plants from the selected recipient plant cells; and identifying a fertile transgenic plant that is tolerant to glyphosate.

In another aspect of the invention is a fertile glyphosate tolerant transgenic plant that contains a plant expression cassette having an aspartic acid at position 8 and an isoleucine or leucine at position 102 that is crossed to another plant to provide progeny that are tolerant to glyphosate.

In another aspect of the invention is a fertile glyphosate tolerant transgenic plant that contains a plant expression cassette having a modified plant EPSPS gene encoding an EPSPS protein having a glutamic acid at position 68, and a cysteine at position 101 that is crossed to another plant to provide progeny that are tolerant to glyphosate.

In another aspect of the invention, there is provided a method for controlling weeds in a field of crop plants, wherein the field of crop plants is treated with an effective amount of a glyphosate containing herbicide and the crop plants contain a plant expression cassette having a modified EPSPS gene encoding an EPSPS protein having an aspartic acid at position 68, and an isoleucine or leucine at position 102.

In another aspect of the invention, there is provided a method for controlling weeds in a field of crop plants, wherein the field of crop plants is treated with an effective amount of a glyphosate containing herbicide and the crop plants contain a plant expression cassette having a modified EPSPS gene encoding an EPSPS protein having a glutamic acid at position 68, and a cysteine at position 101.

In another aspect of the invention, there is provided an isolated modified EPSPS DNA molecule encoding a glyphosate tolerant EPSPS protein having an aspartic acid at position 68, a cysteine at position 101 and an isoleucine or leucine at position 102.

BRIEF DESCRIPTION OF THE DRAWINGS

FIGS. 1A and 1B. Polypeptide alignment of maize EPSPSs (wild-type and mutants) including the following sequences:
TIPT (SEQ ID NO: 9)
TIPA (SEQ ID NO: 10)
TIPS (SEQ ID NO: 11)
Maize (SEQ ID NO: 5)
ADGC (SEQ ID NO: 6)
ADGCTI (SEQ ID NO: 7)
ADTI (SEQ ID NO: 8)

FIG 2. Polypeptide alignment of various wild-type EPSPSs including the following sequences:
*Petunia* (SEQ ID NO: 14)
Soybean 9SEQ ID NO: 12)
Maize (SEQ ID NO: 5)
*E. coli* (SEQ ID NO: 13)

LIST OF SEQUENCES

Figure 3:
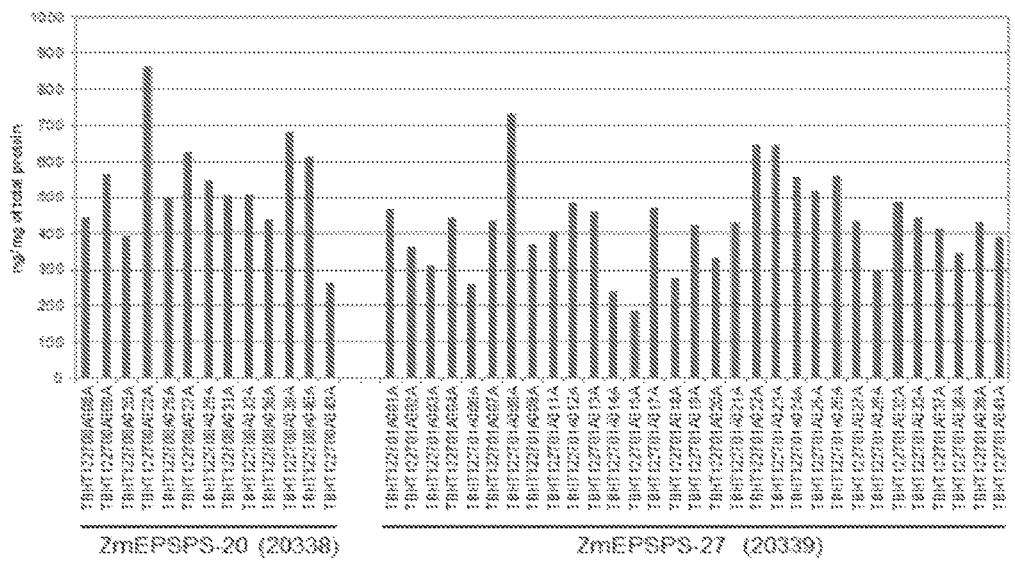
FIG 3. Maize EPSPS gene expression in tobacco events
Figure 4:
FIG 4. Tobacco expressing Maize EPSPS genes, left ZmEPSPS- 20, right Zm EPSPS-27

SEQ ID NO. 1: DNA sequence of maize EPSPS (wild-type)
SEQ ID NO. 2: DNA sequence of maize EPSPS (A[D,E]TI mutant of the present invention)
SEQ ID NO. 3: DNA sequence of maize EPSPS (A[D,E]GC mutant of the present invention)
SEQ ID NO. 4: DNA sequence of maize EPSPS (A[D,E]TIGC mutant of the present invention)
SEQ ID NO. 5: Amino acid sequence of maize EPSPS (wild-type)
SEQ ID NO. 6: Amino acid sequence of maize EPSPS (A[D,E]TI mutant of the present invention)
SEQ ID NO. 7: Amino acid sequence of maize EPSPS (A[D,E]GC mutant of the present invention)
SEQ ID NO. 8: Amino acid sequence of maize EPSPS (A[D,E]TIGC mutant of the present invention)

DETAILED DESCRIPTION OF THE INVENTION

The present invention is drawn to compositions and methods for regulating herbicide resistance in organisms, particularly in plants or plant cells. The methods involve transforming organisms with nucleotide sequences encoding the Class I glyphosate resistance EPSPS genes of the invention. The nucleotide sequences of the invention are useful for preparing plants that show increased tolerance to the herbicide glyphosate. Thus, transformed bacteria, plants, plant cells, plant tissues and seeds are provided. Compositions include nucleic acids and proteins relating to herbicide tolerance in microorganisms and plants as well as transformed bacteria, plants, plant tissues and seeds. Nucleotide sequences of the Class I glyphosate resistance EPSPS genes and the amino acid sequences of the proteins encoded thereby are disclosed. The sequences find use in the construction of expression vectors for subsequent transformation into plants of interest, as probes for the isolation of other glyphosate resistance genes, as selectable markers, and the like.

It is possible to produce glyphosate tolerant plants by inserting into the plant genome a DNA molecule that causes the production of higher levels of wild-type EPSPS (U.S. Pat. No. 4,940,835; Shah et al., Science 233:478-481, 1986). Glyphosate tolerance can be achieved by the expression of EPSPS variants or mutants that have lower affinity for glyphosate and therefore retain their catalytic activity in the presence of glyphosate. Examples include aroA P-S (U.S. Pat. No. 5,094,945), CP4 EPSPS (U.S. Pat. No. 5,633,435), maize TIPS (U.S. Pat. No. 6,040,497), 101/192 and 101/144 variants (U.S. Pat. No. 5,866,775 and U.S. Pat. No. 6,225,112, Howe et al., Mol. Breeding 10:153-164, 2002), 102/106 variants (U.S. Pat. No. 7,723,575) and Class III variants (U.S. Pat. Nos. 7,534,937, 7,405,347, 7,538,262 and associated patents). For example, glyphosate tolerance has been genetically engineered into corn (U.S. Pat. Nos. 5,554,798, 6,040,497), wheat (Zhou et al. Plant Cell Rep. 15:159-163, 1995), soybean (WO 9200377), cotton (WO 0234946), and canola (WO 9204449).

Variants of the wild-type EPSPS enzyme have been isolated that are glyphosate-resistant as a result of alterations in the EPSPS amino acid coding sequence (Kishore et al., Annu. Rev. Biochem. 57:627-663, 1988; Schulz et al., Arch. Microbiol. 137:121-123, 1984; Sost et al., FEBS Lett. 173: 238-241, 1984; Kishore et al., In "Biotechnology for Crop Protection" ACS Symposium Series No. 379. eds. Hedlin et al., 37-48, 1988). These variants typically have a higher Ki for glyphosate than the wild-type EPSPS enzyme that confers the glyphosate-tolerant phenotype, but these variants are also characterized by a high Km for PEP that makes the enzyme kinetically less efficient. For example, the apparent Km for PEP and the apparent Ki for glyphosate for the native EPSPS from *E. coli* are 10 µM and 0.5 µM while for a glyphosate-resistant isolate having a single amino acid substitution of an alanine for the glycine at position 96 these values are 220 µM and 4.0 mM, respectively.

The genes of the present invention are Class I EPSPS genes. There are known mutations within Class I EPSPS genes that can render the gene resistant to glyphosate. U.S. Pat. No. 6,040,497 reports that the Class I EPSPS variant, known as the TIPS mutation (a substitution of isoleucine for threonine at amino acid position 102 and a substitution of serine for proline at amino acid position 106) comprises two mutations that when introduced into the polypeptide sequence of Zea mays EPSPS confers glyphosate resistance to the enzyme. Transgenic plants containing this mutant enzyme are tolerant to glyphosate. Identical mutations may be made in the genes encoding glyphosate sensitive EPSPS enzymes from other sources to create glyphosate resistant enzymes, such as soybean and rice.

Additional Class I mutants are described in U.S. Pat. No. 7,723,575. This patent discloses that additional amino acids can be substituted at the same 102 and 106 positions found in the TIPS mutant, particularly, the threonine at position 102 can be substituted with either isoleucine or leucine and the P at position 106 can be substituted with either threonine or alanine. Both the TIPS mutant and the mutants described within the U.S. Pat. No. 7,723,575 patent require substitutions at position 106 in order to achieve glyphosate tolerance.

In vitro site-directed mutagenesis of DNA molecules have clearly demonstrated utility for introducing specific changes in a DNA sequence of a genome and other methods under development may also provide in situ site-directed mutagenesis methods (US Patent Pub. 20020151072). These methods may be used to generate the DNA coding sequences that encode for the glyphosate resistant EPSPS variants of the present invention in the context of the endogenous host cell EPSPS gene.

The present invention provides amino acid substitutions in a Class I EPSPS that are different from any previously described modified class I EPSPSs. The present invention relates specifically to certain double and triple variants of class I EPSPSs that are glyphosate resistant, but still retain a functional level of PEP substrate binding activity.

The EPSPS enzyme functions in plant chloroplast, therefore, chloroplast transit peptides (CTP) are engineered in a DNA molecule to encode a fusion of the CTP to the N terminus of an EPSPS creating a chimeric molecule. A chimeric polynucleic acid coding sequence is comprised of two or more open reading frames joined in-frame that encode a chimeric protein, for example, a chloroplast transit peptide and an EPSPS enzyme. A chimeric gene refers to the multiple genetic elements derived from heterologous sources operably linked to comprise a gene. The CTP directs the glyphosate resistant enzyme into the plant chloroplast. In the native plant EPSPS gene, chloroplast transit peptide regions are contained in the native coding sequence (for example, CTP2, Klee et al., Mol. Gen. Genet. 210:47-442, 1987). The CTP is cleaved from the EPSPS enzyme at the chloroplast membrane to create a "mature EPSPS or EPSPS enzyme" that refers to the polypeptide sequence of the processed protein product remaining after the chloroplast transit peptide has been removed.

The native CTP may be substituted with a heterologous CTP during construction of a transgene plant expression cassette. Many chloroplast-localized proteins, including EPSPS, are expressed from nuclear genes as precursors and are targeted to the chloroplast by a chloroplast transit peptide (CTP) that is removed during the import steps. Examples of other such chloroplast proteins include the small subunit (SSU) of ribulose-1,5,-bisphosphate carboxylase (rubisco), ferredoxin, ferredoxin oxidoreductase, the light-harvesting complex protein I and protein II, and thioredoxin F. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as, the *Arabidopsis thaliana* EPSPS CTP (Klee et al., Mol. Gen. Genet. 210:437-442 (1987), and the *Petunia hybrida* EPSPS CTP (della-Cioppa et al., Proc. Natl. Acad. Sci. USA 83:6873-6877 (1986) has been shown to target heterologous EPSPS protein to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. Nos. 5,627,061, 5,633,435, 5,312,910, EP 0218571, EP 189707, EP 508909, and EP 924299). Those skilled in the art will recognize that various chimeric constructs can be made that utilize the functionality of a particular CTP to import glyphosate resistant EPSPS enzymes into the plant cell chloroplast.

Modification and changes may be made in the structure of the DNA polynucleotides of the invention and still obtain a DNA molecule that transcribes an mRNA that encodes the modified functional EPSPS protein of the present invention. The amino acid substitutions disclosed herein provide an improved characteristic to the protein, for example, enhanced glyphosate resistant EPSP synthase. Amino-acid substitutions or amino-acid variants, are preferably substitutions of a single amino-acid residue for another amino-acid residue at one or more positions within the protein. Substitutions, deletions, insertions or any combination thereof can be combined to arrive at a final construct. The present invention involves the substitution of amino acids in a class I EPSPS protein to provide a new feature of the protein, such as, glyphosate resistance.

It is known that the genetic code is degenerate. The amino acids and their RNA codon(s) are listed below in Table 1.

TABLE 1

Amino acids and the RNA codons that encode

| Amino Acid Full name; 3 letter code; 1 letter code | Codons |
|---|---|
| Alanine; Ala; A | GCA GCC GCG GCU |
| Cysteine; Cys; C | UGC UGU |
| Aspartic acid; Asp; D | GAC GAU |
| Glutamic acid; Glu; E | GAA GAG |
| Phenylalanine; Phe; F | UUC UUU |
| Glycine; Gly; G | GGA GGC GGG GGU |
| Histidine; His; H | CAC CAU |
| Isoleucine; Ile; I | AUA AUC AUU |
| Lysine; Lys; K | AAA AAG |
| Leucine; Leu; L | UUA UUG CUA CUC CUG CUU |
| Methionine; Met; M | AUG |
| Asparagine; Asn; N | AAC AAU |
| Proline; Pro; P | CCA CCC CCG CCU |
| Glutamine; Gln; Q | CAA CAG |
| Arginine; Arg; R | AGA AGG CGA CGC CGG CGU |
| Serine; Ser; S | AGC AGU UCA UCC UCG UCU |
| Threonine; Thr; T | ACA ACC ACG ACU |
| Valine; Val; V | GUA GUC GUG GUU |
| Tryptophan; Trp; W | UGG |
| Tyrosine; Tyr; Y | UAC UAU |

The codons are described in terms of RNA bases, for example adenine, uracil, guanine and cytosine, it is the mRNA that is directly translated into polypeptides. It is understood that when designing a DNA polynucleotide for use in a construct, the DNA bases would be substituted, for example, thymine instead of uracil. Codon refers to a sequence of three nucleotides that specify a particular amino acid. Codon usage or "codon bias" refers to the frequency of use of codons encoding amino acids in the coding sequences of organisms. A codon usage table would be consulted when selecting substituting codons for an artificial DNA sequence. The sequence of codons provides a coding sequence that refers to the region of continuous sequential nucleic acid triplets encoding a protein, polypeptide, or peptide sequence. The term "encoding DNA" refers to chromosomal DNA, plasmid DNA, cDNA, or artificial DNA polynucleotide that encodes any of the proteins discussed herein. "Plasmid" refers to a circular, extrachromosomal, self-replicating piece of DNA.

The term "endogenous" refers to materials originating from within an organism or cell. "Exogenous" refers to materials originating from outside of an organism or cell. This typically applies to nucleic acid molecules used in producing transformed or transgenic host cells and plants.

The term "genome" as it applies to bacteria encompasses the chromosome, plasmids, and other extrachromosomal DNA within a bacterial host cell. Encoding nucleic acids of the present invention introduced into bacterial host cells can therefore be either chromosomally-integrated, plasmid-localized, part of a bacterial artificial chromosome (BAC), a cosmid, or bacteriophage sequences. The term "genome" as it applies to plant cells encompasses not only chromosomal DNA found within the nucleus, but organelle DNA found within subcellular components of the cell. The term "gene" refers to polynucleic acids that comprise chromosomal DNA, plasmid DNA, cDNA, an artificial DNA polynucleotide, or other DNA that is transcribed into an RNA molecule, wherein the RNA may encode a peptide, polypeptide, or protein, and the genetic elements flanking the coding sequence that are involved in the regulation of expression of the mRNA or polypeptide of the present invention. A "fragment" of a gene is a portion of a full-length polynucleic acid molecule that is of at least a minimum length capable of transcription into a RNA, translation into a peptide, or useful as a probe or primer in a DNA detection method.

Polynucleic acids of the present invention introduced into plant cells can therefore be either chromosomally-integrated or organelle-localized. The modified EPSPSs of the present invention are targeted to the chloroplast or plastid by a transit peptide located at the N-terminus of the coding sequence. Alternatively, the gene encoding the modified EPSPSs may be integrated into the chloroplast genome, thereby eliminating the need for a chloroplast transit peptide.

"Heterologous DNA" sequence refers to a polynucleotide sequence that originates from a foreign source or species or, if from the same source, is modified from its original form. "Homologous DNA" refers to DNA from the same source as that of the recipient cell.

"Hybridization" refers to the ability of a strand of nucleic acid to join with a complementary strand via base pairing. Hybridization occurs when complementary sequences in the two nucleic acid strands bind to one another. The nucleic acid probes and primers of the present invention hybridize under stringent conditions to a target DNA sequence. Any conventional nucleic acid hybridization or amplification method can be used to identify the presence of DNA from a transgenic event in a sample. A transgenic "event" is produced by transformation of a plant cell with heterologous DNA, i.e., a nucleic acid construct that includes a transgene of interest; regeneration of a population of plants resulting from the insertion of the transgene into the genome of the plant cell, and selection of a particular plant characterized by insertion into a particular genome location. The term "event" refers to the original transformant plant and progeny of the transformant that include the heterologous DNA. The term "event" also includes progeny produced by a sexual outcross between the event and another plant that wherein the progeny includes the heterologous DNA. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., Molecular Cloning—A Laboratory Manual, 2nd. ed., Cold Spring Harbor Laboratory, Cold Spring Harbor, N.Y. (1989), herein referred to as Sambrook et al., (1989), and by Haymes et al., In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (such as, to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa, (Nucl. Acids Res. 12:203-213, 1984); and Wetmur and Davidson, (J. Mol. Biol. 31:349-370, 1988). Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, for example, one will select relatively low salt and/or high temperature conditions, such as provided by about 0.02 M to about 0.15 M NaCl at temperatures of about 50° C. to about 70° C. A stringent condition, for example, is to wash the hybridization filter at least twice with high-stringency wash buffer (0.2× SSC, 0.1% SDS, 65° C.). Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA molecules via hybridization is well known to those of skill in the art, and the teachings of U.S. Pat. Nos. 4,965,188 and 5,176,995 are exemplary of the methods of hybridization analyses.

"Identity" refers to the degree of similarity between two polynucleic acid or protein sequences. An alignment of the two sequences is performed by a suitable algorithm. One widely used and accepted computer program for performing sequence alignments is CLUSTALW v1.6 (Thompson, et al. Nucl. Acids Res., 22: 4673-4680, 1994), although others are commonly used. The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between 200 and 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity. In addition to identity positions, consensus positions are also commonly scored. Consensus amino acids are those known to have similar amino acid properties such as charge, size, polarity, and aromaticity.

"Intron" refers to a genetic element that is a portion of a gene not translated into protein, even though it is transcribed into RNA, the intron sequence being "spliced out" from the mature messenger RNA.

An "isolated" nucleic acid molecule is substantially separated away from other nucleic acid sequences with which the nucleic acid is normally associated, such as, from the chromosomal or extrachromosomal DNA of a cell in which the nucleic acid naturally occurs. A nucleic acid molecule is an isolated nucleic acid molecule when it comprises a transgene or part of a transgene present in the genome of another organism. The term also embraces nucleic acids that are biochemically purified so as to substantially remove contaminating nucleic acids and other cellular components. The term "transgene" refers to any polynucleic acid molecule normative to a cell or organism transformed into the cell or organism. "Transgene" also encompasses the component parts of a native plant gene modified by insertion of a normative polynucleic acid molecule by directed recombination or site specific mutation.

"Isolated." "Purified." "Homogeneous" polypeptides. A polypeptide is "isolated" if it has been separated from the cellular components (nucleic acids, lipids, carbohydrates, and other polypeptides) that naturally accompany it or that is chemically synthesized or recombinant. A polypeptide molecule is an isolated polypeptide molecule when it is expressed from a transgene in another organism. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Proteins can be purified by any of the means known in the art, for example as described in Guide to Protein Purification, ed. Deutscher. Meth. Enzymol. 185, Academic Press, San Diego, 1990; and Scopes, Protein Purification: Principles and Practice, Springer Verlag, New York, 1982.

The term "native" generally refers to a naturally-occurring ("wild-type") polynucleic acid or polypeptide. However, in the context of the present invention a modification of a native isolated polynucleotide and polypeptide has occurred to provide a variant polypeptide with a particular phenotype, for example, amino acid substitution in a native glyphosate sensitive EPSPS to provide a glyphosate resistant EPSPS. The polynucleotide modified in this manner is normative with respect to the genetic elements normally found linked to a naturally occurring unmodified polynucleotide.

Using well-known methods, the skilled artisan can readily produce nucleotide and amino acid sequence variants of genes and proteins that provide a modified gene product. For example, "variant" DNA molecules of the present invention are DNA molecules containing changes in an EPSPS coding sequence, such as, changes that include one or more nucleotides of a native EPSPS coding sequence being deleted, added, and/or substituted, such that the variant EPSPS gene encodes a modified protein that retains EPSPS activity and is now resistant to glyphosate herbicide. Variant DNA molecules can be produced, for example, by standard DNA mutagenesis techniques or by chemically synthesizing the variant DNA molecule or a portion thereof. Methods for chemical synthesis of nucleic acids are discussed, for example, in Beaucage et al., Tetra. Letts. 22:1859-1862 (1981), and Matteucci et al., J. Am. Chem. Soc. 103:3185-(1981). Chemical synthesis of nucleic acids can be performed, for example, on automated oligonucleotide synthesizers. Such variants preferably do not change the reading frame of the protein-coding region of the nucleic acid. The present invention also encompasses fragments of a protein that lacks at least one residue of a full-length protein, but that substantially maintains activity of the protein.

A first nucleic-acid molecule is "operably linked" with a second nucleic-acid molecule when the first nucleic-acid molecule is placed in a functional relationship with the second nucleic-acid molecule. For example, a promoter is operably linked to a protein-coding nucleic acid sequence if the promoter affects the transcription or expression of the coding sequence. Generally, operably linked DNA molecules are contiguous and, where necessary to join two protein-coding regions, in reading frame.

The term "plant" encompasses any higher plant and progeny thereof, including monocots (for example, corn, rice, wheat, barley, etc.), dicots (for example, soybean, cotton, canola, tomato, potato, *Arabidopsis*, tobacco, etc.), gymnosperms (pines, firs, cedars, etc.) and includes parts of plants, including reproductive units of a plant (for example, seeds, bulbs, tubers, fruit, flowers, etc.) or other parts or tissues from that the plant can be reproduced.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to a DNA amplification method that uses an enzymatic technique to create multiple copies of one sequence of nucleic acid (amplicon). Copies of a DNA molecule are prepared by shuttling a DNA polymerase between two amplimers. The basis of this amplification method is multiple cycles of temperature changes to denature, then re-anneal amplimers (DNA primer molecules), followed by extension to synthesize new DNA strands in the region located between the flanking amplimers. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention.

The term "promoter" or "promoter region" refers to a polynucleic acid molecule that functions as a regulatory element, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant DNA construct, as demonstrated by its ability to produce mRNA.

A "recombinant" nucleic acid is made by a combination of two otherwise separated segments of nucleic acid sequence, for example, by chemical synthesis or by the manipulation of isolated segments of polynucleic acids by genetic engineering techniques. The term "recombinant DNA construct" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs may be constructed to be capable of expressing antisense RNAs, or stabilized double stranded antisense RNA in order to inhibit expression of a specific target RNA of interest.

"Resistance" refers to an enzyme that is able to function in the presence of a toxin, for example, naturally occurring glyphosate resistant class II EPSPSs resistant to glyphosate or a modified EPSPS enzyme having catalytic activity that is unaffected by at a herbicide concentration that normally disrupts the same activity in the wild type enzyme, for example, the modified class I EPSPS enzymes of the present invention. An enzyme that has resistance to an herbicide may also have the function of detoxifying the herbicide, for example, phosphinothricin acetyltransferase, and glyphosate oxidoreductase.

"Selectable marker" refers to a polynucleic acid molecule that encodes a protein, which confers a phenotype facilitating identification of cells containing the polynucleic acid molecule. Selectable markers include those genes that confer resistance to antibiotics (for example, ampicillin, kanamycin), resistance to herbicides (for example glyphosate or glufosinate), overcome a particular toxic metabolite (for example phosphomannose isomerase, PMI), complement a nutritional deficiency (for example, uracil, histidine, leucine), or impart a visually distinguishing characteristic (for example, color changes or fluorescence). Useful dominant selectable marker genes include genes encoding antibiotic resistance genes (for example, neomycin phosphotransferase, npt); and herbicide resistance genes (for example, phosphinothricin acetyltransferase, class II EPSPSs and class III EPSPSs, modified class I EPSPSs). A useful strategy for selection of transformants for herbicide resistance is described, for example, in Vasil, Cell Culture and Somatic Cell Genetics of Plants, Vols. I-III, Laboratory Procedures and Their Applications Academic Press, New York (1984).

An "artificial polynucleotide" as used in the present invention is a DNA sequence designed according to the methods of the present invention and created as an isolated DNA molecule for use in a DNA construct that provides expression of a protein in host cells, or for the purposes of cloning into appropriate constructs or other uses known to those skilled in the art. Computer programs are available for these purposes, including but not limited to the "BestFit" or "Gap" programs of the Sequence Analysis Software Package. Genetics Computer Group (GCG). Inc., University of Wisconsin Biotechnology Center, Madison, Wis. 53711. The artificial polynucleotide may be created by a one or more methods known in the art, that include, but are not limited to: overlapping PCR. An artificial polynucleotide as used herein, is non-naturally occurring and can be substantially divergent from other polynucleotides that code for the identical or nearly identical protein.

Expression of a Modified Class I EPSPS Coding Sequence in Plants

DNA constructs are made that contain various genetic elements necessary for the expression of the EPSPS coding sequence in plants. "DNA construct" refers to the heterologous genetic elements operably linked to each other making up a recombinant DNA molecule and may comprise elements that provide expression of a DNA polynucleotide molecule in a host cell and elements that provide maintenance of the construct in the host cell. A plant expression cassette comprises the operable linkage of genetic elements that when transferred into a plant cell provides expression of a desirable gene product. "Plant expression cassette" refers to chimeric DNA segments comprising the regulatory elements that are operably linked to provide the expression of a transgene product in plants. Promoters, leaders, introns, transit peptide encoding polynucleic acids, 3' transcriptional termination regions are all genetic elements that may be operably linked by those skilled in the art of plant molecular biology to provide a desirable level of expression or functionality to a glyphosate resistant class I EPSPS of the present invention. A DNA construct can contain one or more plant expression cassettes expressing the DNA molecules of the present invention or other DNA molecules useful in the genetic engineering of crop plants.

A variety of promoters specifically active in vegetative tissues, such as leaves, stems, roots and tubers, can be used to express the EPSPS polynucleic acid molecules of the present invention. Examples of tuber-specific promoters include, but are not limited to the class I and II patatin promoters (Bevan et al., EMBO J. 8:1899-1906, 1986; Koster-Topfer et al., Mol Gen Genet. 219:390-396, 1989; Mignery et al., Gene. 62:27-44, 1988; Jefferson et al., Plant Mol. Biol. 14: 995-1006, 1990), the promoter for the potato tuber ADPGPP genes, both the large and small subunits; the sucrose synthase promoter (Salanoubat and Belliard, Gene. 60:47-56, 1987; Salanoubat and Belliard, Gene 84: 181-185, 1989); and the promoter for the major tuber proteins including the 22 kd protein complexes and proteinase inhibitors (Hannapel, Plant Physiol. 101:703-704, 1993). Examples of leaf-specific promoters include, but are not limited to the ribulose biphosphate carboxylase (RBCS or RuBISCO) promoters (see, for example, Matsuoka et al., Plant J. 6:311-319, 1994); the light harvesting chlorophyll a/b binding protein gene promoter (see, for example, Shiina et al., Plant Physiol. 115:477-483, 1997; Casal et al., Plant Physiol. 116:1533-1538, 1998); and the *Arabidopsis thaliana* myb-related gene promoter (Atmyb5) (Li et al., FEBS Lett. 379:117-121, 1996). Examples of root-specific promoter include, but are not limited to the promoter for the acid chitinase gene (Samac et al., Plant Mol. Biol. 25:587-596, 1994); the root specific subdomains of the CaMV35S promoter that have been identified (Lam et al., Proc. Natl. Acad. Sci. (U.S.A.) 86:7890-7894, 1989); the ORF13 promoter from *Agrobacterium rhizogenes* that exhibits high activity in roots (Hansen et al., Mol. Gen. Genet. 254:337-343 (1997); the promoter for the tobacco root-specific gene TobRB7 (Yamamoto et al., Plant Cell 3:371-382, 1991); and the root cell specific promoters reported by Conkling et al. (Conkling et al., Plant Physiol. 93:1203-1211, 1990).

Another class of useful vegetative tissue-specific promoters is meristematic (root tip and shoot apex) promoters. For example, the "SHOOTMERISTEMLESS" and "SCARECROW" promoters, which are active in the developing shoot or root apical meristems can be used (Di Laurenzio et al., Cell 86:423-433, 1996; Long, Nature 379:66-69, 1996). Another example of a useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, for example, Enjuto et al., Plant Cell. 7:517-527, 1995). Also another example of a useful promoter is that which controls the expression of knl-related genes from maize and other species that show meristem-specific expression (see, for example, Granger et al., Plant Mol. Biol. 31:373-378, 1996; Kerstetter et al., Plant Cell 6:1877-1887, 1994; Hake et al., Philos. Trans. R. Soc. Lond. B. Biol. Sci. 350:45-51, 1995). Another example of a meristematic promoter is the *Arabidopsis thaliana* KNAT1 promoter. In the shoot apex. KNAT1 transcript is localized primarily to the shoot apical meristem; the expression of KNAT1 in the shoot meristem decreases during the floral transition and is restricted to the cortex of the inflorescence stem (see, for example, Lincoln et al., Plant Cell 6:1859-1876, 1994).

Suitable seed-specific promoters can be derived from the following genes: MAC1 from maize (Sheridan et al., Genetics 142:1009-1020, 1996; Cat3 from maize (GenBank No. L05934, Abler et al., Plant Mol. Biol. 22:10131-1038, 1993); viviparous-1 from *Arabidopsis* (Genbank No. U93215); Atmycl from *Arabidopsis* (Urao et al., Plant Mol. Biol. 32:571-57, 1996; Conceicao et al., Plant 5:493-505, 1994); napA from *Brassica napus* (GenBank No. J02798); the napin gene family from *Brassica napus* (Sjodahl et al., Planta 197:264-271, 1995, and others (Chen et al., Proc. Natl. Acad. Sci. 83:8560-8564, 1986).

The ovule-specific promoter for BEL1 gene can also be used (Reiser et al. Cell 83:735-742, 1995, GenBank No. U39944; Ray et al, Proc. Natl. Acad. Sci. USA 91:5761-5765, 1994). The egg and central cell specific MEA (FIS1) and FIS2 promoters are also useful reproductive tissue-specific promoters (Luo et al., Proc. Natl. Acad. Sci. USA, 97:10637-10642, 2000; Vielle-Calzada, et al., Genes Dev. 13:2971-2982, 1999).

A maize pollen-specific promoter has been identified in maize (Guerrero et al., Mol. Gen. Genet. 224:161-168, 1990). Other genes specifically expressed in pollen have been described (see, for example, Wakeley et al., Plant Mol. Biol. 37:187-192, 1998; Ficker et al., Mol. Gen. Genet. 257:132-142, 1998; Kulikauskas et al., Plant Mol. Biol. 34:809-814, 1997; Treacy et al., Plant Mol. Biol. 34:603-611, 1997).

It is recognized that additional promoters that may be utilized are described, for example, in U.S. Pat. Nos. 5,378, 619, 5,391,725, 5,428,147, 5,447,858, 5,608,144, 5,608,144, 5,614,399, 5,633,441, 5,633,435, and 4,633,436. It is further recognized that the exact boundaries of regulatory sequences may not be completely defined, DNA fragments of different lengths may have identical promoter activity.

The translation leader sequence means a DNA molecule located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and *petunia* heat shock protein leaders, plant virus coat protein leaders, plant rubisco gene leaders among others (Turner and Foster, Molecular Biotechnology 3:225, 1995).

The "3' non-translated sequences" means DNA sequences located downstream of a structural polynucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3'; Fraley et al., Proc. Natl. Acad. Sci. USA 80: 4803-4807, 1983). The use of different 3' non-translated sequences is exemplified by Ingelbrecht et al., Plant Cell 1:671-680, 1989.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al. (1989).

The DNA construct of the present invention may be introduced into the genome of a desired plant host by a variety of conventional transformation techniques that are well known to those skilled in the art. "Transformation" refers to a process of introducing an exogenous polynucleic acid molecule (for example, a DNA construct, a recombinant polynucleic acid molecule) into a cell or protoplast and that exogenous polynucleic acid molecule is incorporated into a host cell genome or an organelle genome (for example, chloroplast or mitochondria) or is capable of autonomous replication. "Transformed" or "transgenic" refers to a cell, tissue, organ, or organism into which a foreign polynucleic acid, such as a DNA vector or recombinant polynucleic acid molecule. A "transgenic" or "transformed" cell or organism also includes progeny of the cell or organism and progeny produced from a breeding program employing such a "transgenic" plant as a parent in a cross and exhibiting an altered phenotype resulting from the presence of the foreign polynucleic acid molecule.

Methods of transformation of plant cells or tissues include, but are not limited to Agrobacterium mediated transformation method and the Biolistics or particle-gun mediated transformation method. Suitable plant transformation vectors for the purpose of Agrobacterium mediated transformation include-those elements derived from a tumor inducing (Ti) plasmid of Agrobacterium tumefaciens, for example, right border (RB) regions and left border (LB) regions, and others disclosed by Herrera-Estrella et al., Nature 303:209 (1983); Bevan, Nucleic Acids Res. 12:8711-8721 (1984); Klee et al., Bio-Technology 3(7):637-642 (1985). In addition to plant transformation vectors derived from the Ti or root-inducing (Ri) plasmids of Agrobacterium, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

DNA constructs can be prepared that incorporate the class I EPSPS variant coding sequences of the present invention for use in directing the expression of the sequences directly from the host plant cell plastid. Examples of such constructs suitable for this purpose and methods that are known in the art and are generally described, for example, in Svab et al., Proc. Natl. Acad. Sci. USA 87:8526-8530, (1990) and Svab et al., Proc. Natl. Acad. Sci. USA 90:913-917 (1993) and in U.S. Pat. No. 5,693,507. It is contemplated that plastid transformation and expression of the class I EPSPS variants of the present invention will provide glyphosate tolerance to the plant cell.

When adequate numbers of cells containing the exogenous polynucleic acid molecule encoding polypeptides from the present invention are obtained, the cells can be cultured, then regenerated into whole plants. "Regeneration" refers to the process of growing a plant from a plant cell (for example, plant protoplast or explant). Such regeneration techniques rely on manipulation of certain phytohormones in a tissue culture growth medium, typically relying on a biocide and/or herbicide marker that has been introduced together with the desired nucleotide sequences. Choice of methodology for the regeneration step is not critical, with suitable protocols being available for hosts from Leguminoseae (for example, alfalfa, soybean, clover), Umbelliferae (carrot, celery, parsnip), Cruciferae (for example, cabbage, radish, canola/rapeseed), Cucurbitaceae (for example, melons and cucumber), Gramineae (for example, wheat, barley, rice, maize), Solanaceae (for example, potato, tobacco, tomato, peppers), various floral crops, such as sunflower, and nut-bearing trees, such as almonds, cashews, walnuts, and pecans. See, for example, Ammirato et al., Handbook of Plant Cell Culture-Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone. Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Biotechnology 8:736-740 (1990). Such regeneration techniques are described generally in Klee et al., Ann. Rev. Plant Phys. 38:467-486 (1987).

The development or regeneration of transgenic plants containing the exogenous polynucleic acid molecule that encodes a polypeptide of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants.

Plants that can be made to have enhanced glyphosate tolerance by practice of the present invention include, but are not limited to, Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, *eucalyptus*, fennel, figs, forest trees, gourd, grape, grapefruit, honey dew, jicama, kiwifruit, lettuce, leeks, lemon, lime, Loblolly pine, mango, melon, mushroom, nut, oat, okra, onion, orange, an ornamental plant, *papaya*, parsley, pea, peach, peanut, pear, pepper, persimmon, pine, pineapple, plantain, plum, pomegranate, poplar, potato, pumpkin, quince, *radiata* pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The following examples are provided to better elucidate the practice of the present invention and should not be interpreted in any way to limit the scope of the present invention. Those skilled in the art will recognize that various modifications, additions, substitutions, truncations, etc., can be made to the methods and genes described herein while not departing from the spirit and scope of the present invention.

EXAMPLES

Example 1

Novel Glyphosate Tolerant Gene Discovery

A random mutagenesis approach was used to search for mutations which could render maize EPSPS glyphosate tolerant. Five mutant libraries were created with increasing error rates. In order to screen through the large mutant library, a surrogate system using *Escherichia coli* was employed as a high-throughput, in vivo assay. This screening assay succeeded in identifying the active EPSPS enzymes, reducing the number of mutations to be tested in maize from thousands to less than one hundred. Comparison of the active mutants showed that most were double amino acid mutations and that there was significant overlap between different mutants. Twelve mutations that persisted through different error rates were selected for testing in maize. These mutations are listed in Table 2.

TABLE 2

Description of the ZmEPSPS mutations

| Mutant | nt Changes Site 1 | nt Changes Site 2 | aa Changes aa | aa Changes aa |
|---|---|---|---|---|
| 1 | 172 (G-A) | 422 (A-G) | A59T | K142R |
| 2 | 446 (G-T) | | C150F | |
| 3 | 380 (G-A) | | R128H | |
| 4 | 232 (G-T) | 380 (G-A) | V79F | R128H |
| 5 | 232 (G-A) | 242 (G-A) | V79I | G82D |
| 6 | 283 (C-G) | | L96V | |
| 7 | 296 (A-G) | | N100S | |
| 8 | 203 (C-A), 204 (T-A) | 301 (G-T), 303 (A-C) | A68E | G101C |
| 9 | 331 (G-A) | | V112I | |
| 10 | 212 (C-T) | 439 (G-C) | A72V | V148L |
| 11 | 455 (G-A) | | G153D | |
| 12 | 341 (C-T) | | A115V | |
| 13 | 203 (C-A) | 305 (C-T) | A68D | T102I |

Example 2

Creation of ZmEPSPS Genes for Plant Transformation 13 mutants of maize EPSPS (ZmEPSPS) gene were selected from the screening for glyphosate tolerance in *E. coli* Site directed mutagenesis PCR reactions were used to create all 13 mutants with soybean codon optimized synthetic wild type ZmEPSPS gene as a template. Mutations were introduced in the complementary PCR primers. The PCR amplified mutant EPSPS genes were cloned in between the CMP-02 promoter and nos terminator in a binary vector for plant transformation. The final vectors were introduced into *Agrobacterium* EHA101 strain for transformation.

Example 3

Screening Maize Mutants Using Tobacco Regeneration System

The efficacy of maize mutant genes (Table 2) were tested using a tobacco leaf discs transformation/regeneration system. Following *Agrobacterium*-mediated transformation, the explants were incubated on regeneration medium containing 50 nM glyphosate and 200 mg/L Timentin. Regeneration of explants on glyphosate media is dependent on the efficacy of the mutant gene to provide tolerance to glyphosate. If the mutant is weak or does not work, no regeneration is observed. Thus, by using the ability to regenerate on glyphosate media, two mutant genes, ZmEPSPS-20 (contains Table 2 mutant #13; SEQ ID NO. 6) and ZmEPSPS-27 (contains Table 2 mutant #8; SEQ ID NO. 7) were identified as tolerant mutants. Additionally, a third mutant comprising the mutations of mutant #8 and #13 is possible resulting in an A[D,E]TIGC mutant.

Example 4

Tobacco Glyphosate Tolerant Event Production

The leaf disc tobacco transformation method (Horsch et al., 1985) was employed using the EHA101 *Agrobacterium* strain. 0.5 cm² leaf discs were prepared from in vitro grown SR1 *Nicotana tabacum* plants and were submerged in *Agrobacterium* suspension culture with an optical density of 0.5 for 15 min. The discs were blotted dry on a sterile Whatman filter paper. Following *Agrobacterium* treatment, the leaf discs were cultured on media containing 100 uM Touchdown and 200 mg/L Timentin to select transformants. Regenerating putative transgenic shoots were cultured on root inducing media containing 100 uM Touchdown and 200 mg/L Timentin. Shoots with good roots were tested for the presence of transgenes using a Taqman assay. Taqman positive plants were transferred to soil and grown to maturity in the greenhouse. Transformation frequency for each mutant by the following formula (Data in Table 3):

Total number of Taqman positive events obtained/
Total number explants used)×100

TABLE 3

Stable transformation frequency in tobacco with ZmEPSPS gene as selectable marker.

| Contruct | Selectable marker | Number of explants | Number of transgenic events | Transformation frequency (%) |
|---|---|---|---|---|
| 18947 | ZmEPSPS-20 | 96 | 33 | 34.4 |
| 19087 | ZmEPSPS-27 | 54 | 26 | 48.1 |

The level of ZmEPSPS expression in tobacco transformants is shown in FIG. 3.

Example 5

Testing the Efficacy of the Mutant Genes in Tobacco

T0 transgenic tobacco plants were grown on soil for 4 weeks in Conviron growth chambers. These plants were sprayed with 2×, 4× and 8× Touchdown herbicide at 2×, 4× and 8× field rate (1× field rate=1680 g AE/Ha), respectively, and the herbicide damage was assessed 2 weeks post treatment. Tobacco events harboring the ZmEPSPS-20 and ZmEPSPS-27 events were completely tolerant to 2× and 4× field rates and showed only minor damage to 4× field rates. Results depicted in Table 4.

TABLE 4

Results of spray with glyphosate on ZmEPSPS mutant containing tobacco

| Selectable marker | Rate | Damage |
|---|---|---|
| ZmEPSPS-20 | 2X | No damage |
| ZmEPSPS-27 | 2X | No damage |
| ZmEPSPS-20 | 4X | No damage |
| ZmEPSPS-27 | 4X | No damage |
| ZmEPSPS-20 | 8X | Minor damage at shoot apex |
| ZmEPSPS-27 | 8X | Minor damage, some deformed leaves |

Example 6

Soybean Transformation

Matured soybean seeds (cv. Jack) were sterilized overnight in a fume hood with the fume generated by mixing 100 ml of commercial bleach with 7 ml of hydrochloric acid. Sterile seeds were germinated on germination media for 18 hrs. Explants were prepared by following the method described in the patent application (US 2004/0034889).

Seed coat was excised and removed. One cotyledon was removed by snapping off, leaving the embryonic axis attached to the other cotyledon. The primary leaves on the embryonic axis were removed, the hypocotyl was trimmed and the shoot apex was wounded by gently inserting the tip of the scalpel blade. These explants were submerged in 0.6 OD *Agrobacterium* suspension culture for 3 hrs. Following *Agrobacterium* inoculation, the explants were placed on co-cultivation medium and incubated at 23 C for 3 days. The explants were the inserted in recovery medium and incubated for 7 days at 28 C under light with a 16/8 hrs photoperiod. Explants were transferred to regeneration medium containing 75 uM glyphosate and incubated under the same culture room conditions for three weeks. The cotyledon was excised and the explants were inserted into elongation medium containing 50 uM glyphosate and incubated in culture room for three weeks and sub-cultured onto fresh elongation medium every three weeks. Freshly elongating shoots were transferred to fresh elongation medium in plant container and allowed to grow further. Shoots which reached about 3 cm long were transferred to soil and grown in a Conviron growth room. Shoots with good roots were analyzed for the presence of transgenes using a Taqman assay. Taqman positive plants with a good root system were transferred to greenhouse and grown to maturity. Transformation frequency was calculated as with tobacco (Table 5).

TABLE 5

Stable transformation frequency in soybean with ZmEPSPS-20 as selectable marker (Construct 20492).

| Transformation experiment | Number of explants | Number of transgenic events | Transformation frequency (%) |
|---|---|---|---|
| 1 | 103 | 12 | 11.65 |
| 2 | 105 | 6 | 5.71 |
| 3 | 104 | 0 | 0.00 |
| 4 | 131 | 10 | 7.63 |
| 5 | 116 | 1 | 0.86 |
| 6 | 120 | 11 | 9.17 |
| 7 | 115 | 10 | 8.70 |

REFERENCES

Horsch R B, Fry J E, Hoffman N L, Eichholtz D, Rogers S G, Fraley R T (1985). A simple and general method for transferring genes into plants. Science, 227: 1229-1231.

What is claimed:

1. An isolated DNA molecule encoding a modified EPSPS enzyme wherein said enzyme comprises:
   a. a first amino acid substitution from Alanine to Aspartic Acid or Glutamic Acid at the Alanine which corresponds to position 68 of the amino acid sequence of SEQ ID NO: 5; and
   b. a second amino acid substitution from Glycine to Cysteine at the Glycine which corresponds to position 101 of the amino acid sequence of SEQ ID NO:5, and
   c. optionally a third amino acid substitution from Threonine to Isoleucine at the Threonine which corresponds to position 102 of the amino acid sequence of SEQ ID NO:5.

2. The isolated DNA molecule of claim 1, wherein said DNA molecule is derived from *Zea mays*.

3. The isolated DNA molecule of claim 2, wherein said modified EPSPS enzyme comprises a polypeptide sequence selected from the group consisting of: SEQ ID NO. 7 and SEQ ID NO, 8.

4. The isolated DNA molecule of claim 3, wherein said DNA molecule comprises a polynucleotide sequence selected from the group consisting of: SEQ ID NO. 3 and SEQ ID NO. 4.

5. The isolated DNA molecule of claim 1, wherein said DNA molecule is derived from a bacteria genome.

6. A DNA construct comprising a promoter that functions in plant cells operably linked to the isolated DNA molecule of claim 1.

7. The DNA construct of claim 6, wherein said modified EPSPS enzyme comprises a polypeptide sequence selected from the group consisting of: SEQ ID NO. 7 and SEQ ID NO. 8.

8. The DNA construct of claim 6, comprising a DNA molecule selected from the group consisting of SEQ ID NO. 3 and SEQ ID NO. 4.

9. A method of preparing a glyphosate tolerant plant comprising the steps of:
   a. contacting a recipient plant cell with the DNA construct of claim 6, wherein said DNA construct is incorporated into the genome of the recipient plant cell;
   b. regenerating the recipient plant cell into a plant; and
   c. applying an effective dose of glyphosate to the plant, wherein the plant displays a glyphosate tolerant phenotype.

10. The method of claim 9, wherein said modified EPSPS enzyme comprises a polypeptide sequence selected from the group consisting of: SEQ ID NO. 7 and SEQ ID NO. 8.

11. The method of claim 9, wherein said DNA construct comprises a DNA molecule selected from the group consisting of: SEQ ID NO. 3 and SEQ ID NO. 4.

12. A glyphosate tolerant plant or progeny thereof comprising the DNA construct of claim 6.

13. A glyphosate tolerant plant of claim 12, wherein said modified EPSPS enzyme comprises a polypeptide sequence selected from the group consisting of: SEQ ID NO. 7 and SEQ ID NO. 8.

14. A glyphosate tolerant plant of claim 12, wherein the DNA construct comprises an EPSPS coding sequence selected from the group consisting of SEQ ID NO. 3 and SEQ ID NO. 4.

15. A method of controlling weeds in a field of glyphosate tolerant crop plants comprising applying to said field of glyphosate tolerant crop plants an effective dose of a glyphosate containing herbicide, wherein said glyphosate tolerant crop plants contain a DNA construct comprising a promoter that functions in plant cells operably linked to a DNA molecule that encodes a chloroplast transit peptide linked to the isolated DNA molecule of claim 1.

16. The method of claim 15, wherein said modified EPSPS enzyme comprises a polypeptide sequence selected from the group consisting of: SEQ ID NO. 7 and SEQ ID NO. 8.

17. The method of claim 15, wherein said DNA construct comprises a DNA molecule selected from the group consisting of SEQ ID NO. 3 and SEQ ID NO. 4.

18. The isolated DNA molecule of claim 1, wherein said enzyme further comprises an amino acid substitution from Proline to Serine or Threonine or Alanine at the Proline which corresponds to position 106 of the amino acid sequence of SEQ ID NO: 5.

19. A purified EPSPS enzyme comprising:
   a. a first amino acid substitution from Alanine to Aspartic Acid or Glutamic Acid at the Alanine which corresponds to position 68 of the amino acid sequence of SEQ ID NO: 5; and b. a second amino acid substitution from Glycine to Cysteine at the Glycine which corresponds to position 101 of the amino acid sequence of SEQ ID NO:5, and
c. optionally a third amino acid substitution from Threonine to Isoleucine at the Threonine which corresponds to position 102 of the amino acid sequence of SEQ ID NO:5.

* * * * *